United States Patent [19]

Pierschbacher et al.

[11] Patent Number: 5,591,822
[45] Date of Patent: Jan. 7, 1997

[54] HYDROPHOBIC ATTACHMENT SITE FOR ADHESION PEPTIDES

[75] Inventors: Michael D. Pierschbacher, San Diego; Cyril J. Honsik, La Jolla; Lisa B. Dreisbach, Cardiff, all of Calif.

[73] Assignee: La Jolla Cancer Research Foundation, La Jolla, Calif.

[21] Appl. No.: 435,317

[22] Filed: May 5, 1995

Related U.S. Application Data

[63] Continuation of Ser. No. 932,929, Aug. 20, 1992, which is a continuation of Ser. No. 787,318, Oct. 30, 1991, abandoned, which is a continuation of Ser. No. 326,168, Mar. 20, 1989, Pat. No. 5,120,829.

[51] Int. Cl.$^6$ ............ A61K 38/00; A61K 38/04; C07K 5/00; C07K 7/00
[52] U.S. Cl. ........................... 530/326; 514/13
[58] Field of Search .................. 514/2, 12, 13; 530/326

[56] References Cited

U.S. PATENT DOCUMENTS 5,120,829  6/1992  Pierschbacker et al. ............... 530/326

OTHER PUBLICATIONS

Low, *Biochem J.*, vol. 244, pp. 1–13, 1987.

*Primary Examiner*—Avis M. Davenport
*Attorney, Agent, or Firm*—Campbell & Flores LLP

[57] ABSTRACT

The invention provides a method of attaching peptides containing a biologically active site, for example RGD-containing adhesion peptides, to a solid surface through a hydrophobic domain, and peptides so attached. The hydrophobic domain can contain either hydrophobic amino acids, such as leucine, valine, isoleucine or phenylalanine, or fatty acids, such as, for example, myristic acid, palmitic acid, arachidic acid or other fatty acids. Additionally, spacers, such as amino acids, between the hydrophobic domain and the biologically active domain can improve the presentation of the biologically active site. Specific peptides of the invention include $GRGDSPASSKG_4RL_6RNH_2$;
$GRGDSPASSKS_3RL_6RNH_2$; and
$GRGDSPASSKSSKRL_6RNH_2$.

2 Claims, No Drawings

HYDROPHOBIC ATTACHMENT SITE FOR ADHESION PEPTIDES

This application is a continuation of application Ser. No. 07/932,929, filed Aug. 20, 1992, pending which is a continuation of Ser. No. 07/787,318, filed Oct. 30, 1991, now abandoned, which is a continuation of Ser. No. 07/326,168, filed Mar. 20, 1989, now issued as U.S. Pat. No. 5,120,829.

BACKGROUND OF THE INVENTION

This invention relates to peptides and, more specifically, to peptides having a hydrophobic domain to facilitate their attachment to a solid substrate.

A variety of assays and purification techniques require that a ligand, such as a peptide, be immobilized on a solid support. Generally, two methods have been used to accomplish such immobilization. The peptide may be applied to the surface in solution, which is then evaporated off, leaving the peptide dried to the surface. Such non-specific attachment is inefficient for small peptides and applicable only to methods which do not require a large concentration of immobilized peptide, as much will be resolubilized subsequently in the presence of solution. Moreover, because the attachment is non-specific, peptides will be attached in random and variant orientations. Where presentation of a particular active site is critical, such variance can further reduce the specificity of the bound peptide.

In the more common two-step chemical coupling process, the solid surface is first passively coated with a large protein, such as an immunoglobulin or bovine serum albumin. A hetero-bifunctional cross-linking agent, such as SPDP or glutaraldehyde, is attached to the protein and used to capture peptide from solution. Such a method, while time consuming, is currently used, for example, in cell culture procedures which require a high concentration of bound peptide.

It is now recognized that many cell-cell and cell-matrix interactions are mediated by an arginine-glycine-aspartic acid (Arg-Gly-Asp or RGD) amino acid domain which is common to various adhesion proteins. This binding site is recognized by receptors. Synthetic peptides containing such a domain may be used in a variety of applications, including the coating of tissue culture plates or prostheses and immobilization for the purpose of the purification of adhesion receptors on a column. Achieving the attachment of an RGD-containing peptide to the solid substrate entails the same problems as do other peptides. In addition, because the adhesion domain is small, it is important that the domain be accessible to ligands, as by using a spacing group to distance the tripeptide from the surface that is being coated. Moreover, where the coating is for in vivo use, such as with a prosthesis, it is important that the coats be non-immunogenic and non-cytotoxic There thus exists a need for a rapid and reproducible one step-process for attaching peptides, such as RGD containing peptides, to a solid surface. Ideally, such a method should be easy to perform and efficient. In addition, it should preferably result in appropriate presentation of critical epitopes, such as the RGD domain. The present invention satisfies these needs and provides related advantages as well.

SUMMARY OF THE INVENTION

The invention provides a method of attaching peptides containing a biologically active site, for example RGD-containing adhesion peptides, to a solid surface through a hydrophobic domain, and peptides so attached. The hydrophobic domain can contain either hydrophobic amino acids, such as leucine, valine, isoleucine or phenylalanine, or fatty acids, such as, for example, myristic acid, palmitic acid, arachidic acid or other fatty acids. Additionally, spacers, such as amino acids, between the hydrophobic domain and the biologically active domain can improve the presentation of the biologically active site. Specific peptides of the invention include

GRGDSPASSKG$_4$RL$_6$RNH$_2$;

GRGDSPASSKS$_3$RL$_6$RNH$_2$; and

GRGDSPASSKSSKRL$_6$RNH$_2$.

DETAILED DESCRIPTION OF THE INVENTION

The present invention relates to the use of hydrophobic domains, such as hydrophobic amino acids or fatty acids, on peptides to facilitate the attachment of the peptide to solid substrates. Such methods of specifically attaching synthetic peptides using hydrophobic domains is useful for localizing a broad range of synthetic peptides to a variety of surfaces. The methodology is of particular utility with RGD-containing adhesion peptides. The method, which bypasses the conventional two-step chemical coupling process, provides a rapid and reproducible method for presenting the RGD active site, for binding both with specific receptors as well as with specific cell types. Moreover, the coating can be relatively non-immunogenic and non-cytotoxic, particularly when naturally occurring amino acids and fatty acids are used.

RGD is known to comprise the binding site of various extracellular matrix proteins, such as fibronectin. RGD containing peptides coated on a substrate promote cell attachment. Alternatively, in soluble form, RGD containing peptides inhibit attachment or promote detachment of cells from a substrate. The arginine residue can be in the D- or L-configuration. See U.S. Pat. Nos. 4,578,079, 4,614,517 and 4,792,525 and Ser. No. 738,078, all of which are incorporated herein by reference.

A peptide is constructed to have a hydrophobic domain, preferably at the carboxyl terminus of the biologically active site of interest. The hydrophobic domain can comprise either multiple hydrophobic amino acid residues, such as leucine, valine, isoleucine or phenylalanine or fatty acids such as myristate $CH_3(CH_2)_{12}COO^-$, palmitate $CH_3(CH_2)_{12}COO^-$, $CH_3(CH_2)_{12}COO^-$, arachidate $CH_3(CH_2)_{12}COO^-$, etc. In one embodiment, the hydrophobic domain comprises multiple leucine residues, such as L$_6$NH$_2$ or L$_{4N}$H$_2$. Alternatively, amino acid sequences such as phenylalamine, isoleucine or valine may be used.

In order to have sufficient hydrophobicity to facilitate attachment, the hydrophobic domain must have at least the hydrophobicity of the sequence L$_4$. As used herein, "hydrophobic domain" refers to a domain having a hydrophobicity at least equivalent to the degree of hydrophobicity exhibited by the amino acid sequence L$_4$.

The addition of amino acid spacers between the active site and the hydrophobic domain can improve active site presentation. These spacers can be amino acids, for example glycine or serine. Preferably more than one residue is used, such as S$_2$, S$_3$, or G$_4$. In addition, other organic compounds such as sugars, or other carbon containing, non-hydrophobic moieties can be used.

Less specific cell attachment can be achieved using as the attachment site certain positively charged amino acids known to promote attachment, such as arginine, lysine, homoarginine or ornithine in combination with the hydrophobic domain. For example, both $R_6GL_6NH_2$ and $RL_6RNH_2$ have been shown to have some cell attachment promoting activity.

When in solution, the peptide can be used to coat surfaces such as tissue culture apparatus, prosthetic implant devices, columns for cell or receptor isolation and surfaces for ELISA. The surfaces can by hydrophobic or hydrophilic. The hydrophobic domain will adhere to such surfaces spontaneously as it is driven from solution in an aqueous environment. Greater peptide coating can be achieved by drying the peptide solution down onto the surface. Appropriate surfaces include Millicell™-CM, Immobilon™, Polystyrene, Polycarbonate, Teflon (polytetrafluoroethylene), Silicone, Polyurethane, Polylactic Acid, Titanium, Polyethylene, Gortex (expanded polytetrafluorethylene), tooth dentine and cementum.

Where the peptide has cell adhesion promoting activity, the method provides an improved means of cell culture in serum free conditions. This method also has application for prosthetic devices where it is desirable to have cells attach to the implanted device. Additionally by reproducing a natural extracellular matrix binding site on the substrate, the production of cellular proteins requiring such a substrate can be increased. Using a hydrophobic domain in conjunction with an RGD binding site facilitates the isolation of receptors which recognize the RGD site.

The use of naturally occurring amino acids or fatty acids is preferable to other hydrophobic moieties when coating prosthetic devices to be used in humans because they are relatively non-immunogenic and non-toxic.

The following standard abbreviations are used herein to identify amino acid residues.

TABLE I

| Amino Acid | Three-letter Abbreviation | One-letter Symbol |
| --- | --- | --- |
| Alanine | Ala | A |
| Arginine | Arg | R |
| D-Arginine | D-Arg | dR |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V | nMe refers to an n-Methyl group.

All amino acids are in the L-configuration unless otherwise specified.

The following examples are intended to illustrate but do not limit the invention.

EXAMPLE I

PRODUCTION OF THE PEPTIDES

Peptides were synthesized using an automated peptide synthesizer (Model 430A; Applied Biosystems, Foster City, Calif.), using the instructions provided by the manufacturer, and purified by reverse phase HPLC on a Biogel TSK SP-5-PW cation exchange column (Bio-Rad Laboratories, Richmond, Calif.).

EXAMPLE II

ATTACHMENT OF PEPTIDES

The following peptides were tested for their ability to spontaneously adhere to the plastic wells and subsequently promote cell attachment: $XG(R)GDSPASSKL_2NH_2$, $XG(R)GDSPASSKL_4NH_2$, $XG(R)GDSPASSKL_6NH_2$, $XG(R)GDSPASSK_6$, $XG(R)GDSPASSE_6$, where X is $NH_2$, nMe, acetyl or other amino acid. The peptides were solubilized in 70% EtOH at a starting concentration of 1 mg/ml. 200 µl was then added in duplicate to the first two wells of ninety-six well polystyrene microtiter plates that had not been treated for tissue culture. The remaining wells contained 100 µl of 70% EtOH. Taking 100 µl from the 1 mg/ml solution in the first two wells, a serial dilution was performed out to 0.15 µg/well for each peptide. The plates were allowed to dry overnight at 37° C. in the presence of a desiccator.

The following day the peptide coated plates were used in a standard adhesion assay as described in Example III, using MG-63 cells, an osteosarcoma cell line available from American Type Tissue Culture.

EXAMPLE III

CELL ADHESION ASSAY

The plates were washed 1× using PBS, (150 mM NaCl/10 mM sodium phosphate, pH 7.4). The plates were incubated with DMEM (0.1 ml/well) containing bovine serum albumin (BSA 2.5 mg/ml; Sigma Chemical Co., St. Louis, Mo.) for one hour. Two x $10^5$ cells/ml (MG-63) were suspended in DMEM, and BSA (2.5 mg/ml). 100 µl of cell suspension was added per well and the plates are incubated at 37° C. in 7.5% $CO_2$/92.5% air for one hour. Afterwards, the plate was washed once in PBS. Attached cells were then fixed with 3% paraformaldehyde and stained overnight with 1% toluidine blue in 10% formaldehyde. The following day, the excess stain was removed and the plates were washed with $H_2O$; 100 µl of a 1% sodium dodecyl sulfate (SDS) solution was added to each well. The level of cell attachment was then measured, using a kinetic microplate reader (Molecular Devices,) by assessing the optical density at 630 nm.

The results are presented in Table II. $XG(R)GDSPASSKL_6NH_2$ promoted significant cell attachment out to a 3 µg/well. $XG(R)GDSPASSKL_4NH_2$ promoted marginal cell attachment only at the highest concentration of 100 µg/well. The other peptides $nMeG(dR)GDSPASSKL_2NH_2$, $nMeG(dR)GDSPASSK_6$, $nMeG(dR)GDSPASSE_6$ did not promote significant cell attachment (Table II).

TABLE II

| µg/well Peptide | 100 | 50 | 25 | 12 | 6 | 3 | 1.5 |
| --- | --- | --- | --- | --- | --- | --- | --- |
| $K_6$ | 3 | 2 | 2 | 2 | 2 | 3 | 2 |
| $E_6$ | 8 | 5 | 3 | 3 | 2 | 2 | 2 |
| $L_2$ | 6 | 6 | 3 | 2 | 1 | 1 | 1 |
| $L_4$ | 44 | 12 | 16 | 10 | 2 | 1 | 1 |
| $L_6$ | 100 | 76 | 60 | 60 | 60 | 5 | 3 |

EXAMPLE IV

PHENYLALANINE AS A HYDROPHOBIC CARRIER

The hydrophobic attachment of RGD containing peptides can be achieved with other hydrophobic amino acids. The following peptide, nMeG(dR)GDSPASSKRF$_4$RNH$_2$ was solubilized in 70% ETOH and used in an adhesion assay as described previously. This experiment also demonstrated the increase in cell binding by using an S$_3$ spacer on an RF$_6$RNH$_2$ tail. GRGESPS$_8$L$_6$NH$_2$ was used as a negative control, in that RGE is known not to have cell binding activity. The results are presented in Table III.

TABLE III

PHENYLALANINE AS A HYDROPHOBIC DOMAIN

| µg/well | 100 | 50 | 25 | 12 | 6 | 3 | 1.5 |
|---|---|---|---|---|---|---|---|
| nMeGRGDSPASSKS$_3$RF$_6$RNH$_2$ | 69 | 69 | 60 | 66 | 65 | 70 | 70 |
| nMeGRGDSPASSKRF$_6$RNH$_2$ | 70 | 75 | 56 | 52 | 57 | 54 | 50 |
| nMeGRGDSPASSKL$_6$NH$_2$ | 80 | 78 | 58 | 66 | 60 | 56 | 47 |
| nMeGRGDSPASSKRL$_5$RNH$_2$ | 72 | 68 | 58 | 66 | 60 | 44 | 34 |
| nMeGRGDSPASSKRF$_4$RNH$_2$ | 70 | 73 | 60 | 59 | 56 | 50 | 34 |
| GRGESPS$_8$L$_6$NH$_2$ | 27 | 17 | 16 | 10 | 16 | 8 | 3 |

The values represent percentage of maximum binding.

EXAMPLE V

MYRISTIC ACID AS A HYDROPHOBIC CARRIER

Fatty acids can also be used to promote the hydrophobic attachment of RGD containing peptides. Myristic acid was attached to the peptide, nMeG(dR)GDSPASSK via the epsilon amino group of the lysine. Cell attachment activity was determined as in Examples II and III.

TABLE IV

| µg/well | 100 | 50 | 25 | 12 | 6 |
|---|---|---|---|---|---|
| Myristic acid | 33 | 30 | 50 | 75 | 45 |
| nMeGDRGDSPASSKL$_6$-NH$_2$ | 100 | 100 | 100 | 50 | 35 |

The values represent percentage of maximum binding.

EXAMPLE VI

Cell attachment can also be promoted using positive charge alone on a hydrophobic tail, such as the peptide R$_6$GL$_6$. The peptides were coated as in Example II and used in the assay of Example III.

| µg/well | 300 | 150 | 75 | 25 | 12 | 6 |
|---|---|---|---|---|---|---|
| R$_6$GL$_6$ | 70 | 60 | 50 | 50 | 50 | 43 |
| nMeG(dR)GDSPASSKL$_6$NH$_2$ | 100 | 85 | 65 | 50 | 50 | 45 |

The values represent percentage of maximum binding.

EXAMPLE VII

The addition of amino acid spacers between the hydrophobic domain in the RGD binding site enhances the presentation of the RGD peptide for cell binding. The peptides were coated as in Example II, for four hours.

ASSAY 10/14/88

| Peptides 23 µg/well | 10 | 5 | 2.5 | 1.25 | 6 |
|---|---|---|---|---|---|
| nMeG(dR)GDSPASSKS$_4$RL$_6$RNH$_2$ | 57 | 76 | 100 | 92 | 76 |
| nMeG(dR)GDSPASSKS$_2$RL$_6$RNH$_2$ | 34 | 53 | 57 | 46 | 38 |
| nMeG(dR)GDSPASSKL$_6$NH$_2$ | — | 65 | 65 | 12 | 9 |

The values represent percentage of maximum binding.

Although the invention has been described with reference to the presently-preferred embodiment, it should be understood that various modifications can be made by those skilled in the art without departing from the invention. Accordingly, the invention is limited only by the following claims.

We claim:

1. A peptide having the amino acid sequence X-GRGDSPASSK(G)$_4$SR(L)$_6$R-Amide, wherein X is NH$_2$, nMe, acetyl or other amino acid.

2. A peptide having the amino acid sequence Ac-G(dR)GDIPASSK(G)$_4$S(dR)(L)$_6$(dR)-NH$_2$.

* * * * *

UNITED STATES PATENT AND TRADEMARK OFFICE
CERTIFICATE OF CORRECTION

PATENT NO. : 5,591,822
DATED : Jan. 7, 1997
INVENTOR(S) : Pierschbacher et al.

It is certified that error appears in the above-identified patent and that said Letters Patent is hereby corrected as shown below:

In column 1, line 50, please delete "tripepride" and replace therefor --tripeptide--.

Signed and Sealed this

Twenty-seventh Day of March, 2001

*Attest:*

NICHOLAS P. GODICI

*Attesting Officer*     *Acting Director of the United States Patent and Trademark Office*